United States Patent [19]

Menon et al.

[11] Patent Number: 4,680,304

[45] Date of Patent: Jul. 14, 1987

[54] FEED COMPOSITIONS CONTAINING 2-(α-PYRIDYL)-Δ$^2$-HETEROCYCLIC COMPOUNDS

[75] Inventors: Govind K. Menon, Downingtown, Pa.; Winfred J. Sanders, Mt. Laurel, N.J.

[73] Assignee: SmithKline Beckman Corporation, Philadelphia, Pa.

[21] Appl. No.: 710,791

[22] Filed: Mar. 12, 1985

[51] Int. Cl.$^4$ .............................................. A61K 31/44
[52] U.S. Cl. .................................... 514/340; 514/341; 514/342; 514/343; 514/351
[58] Field of Search ............... 514/340, 341, 342, 343, 514/351

[56] References Cited

U.S. PATENT DOCUMENTS 4,249,008  2/1981  Sykes et al. ......................... 546/281
4,339,535  7/1982  Sykes et al. ......................... 535/119

*Primary Examiner*—Frederick E. Waddell
*Attorney, Agent, or Firm*—Mark R. Daniel; Janice E. Williams; Alan D. Lourie

[57] ABSTRACT

Selected 2-(α-pyridyl)-Δ$^2$-heterocyclic compounds are used as active ingredients in animal feed compositions and in methods for increasing the growth or feed efficiency of monogastric animals. An active ingredient for use in this invention is 3,4-dihydro-4-hydroxy-5-(3-hydroxy)-2-pyridinyl)-4-methyl-2H-pyrrole-5-carboxamide.

12 Claims, No Drawings

FEED COMPOSITIONS CONTAINING 2-(α-PYRIDYL)-Δ²-HETEROCYCLIC COMPOUNDS

This invention comprises new animal feed compositions and methods which use a 2-(α-pyridyl)-Δ²-heterocyclic compound as an active ingredient for altering metabolism in the digestive tract of monogastric animals, thereby improving growth and feed efficiency of the animals.

DESCRIPTION OF THE PRIOR ART

Those skilled in the art will recognize that certain of the active ingredients used in this invention are known to the art. For example, one compound is an antibiotic known as EM4940 or siderochelin which has been patented by E. R. Squibb & Sons, Inc.; U.S. Pat. Nos. 4,249,008 and 4,339,535. Other active ingredients are either known to the art in other fields or are prepared as described in the Examples. Certain active ingredients are new compounds.

As far as we are aware, no utility similar to that described herein has been suggested in prior publications.

DESCRIPTION OF THE INVENTION

The animal feed compositions of this invention, which are supplemented by a 2-(α-pyridyl)-Δ²-heterocyclic compound, are fed to monogastric, growing or fattening, meat-producing animals, especially swine and poultry.

For example, it is known to the art that, during assimilation of food, the production of volatile fatty acids and lactic acid in swine should be relatively low in the upper part of the digestive tract. On the other hand, glucose levels should be higher in the upper tract. Lysine is an essential amino acid which is necessary for growth. Therefore, high levels of lysine are also desirable. Often, corn diets, which are naturally low in lysine, are supplemented with lysine.

The compositions and methods of this invention, however, are believed not to operate by inducing a shift of volatile fatty acid production in the upper digestive tract but by a previously unknown, possibly antimicrobial, effect. This is brought about by administering a nontoxic but effective quantity of a selected active ingredient orally to the subject animals to insure that a larger than normal quantity of energy and amino acid units are available for growth to the animals from each unit of food in their diets.

The active ingredients, which are useful in the feed compositions and methods of this invention, are illustrated by the structural formula:

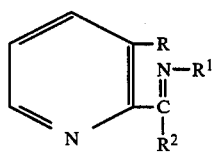

(I)

in which:

R is hydrogen or hydroxy;

$R^1$ is hydrogen or, when also attached to $R^2$, methylene, oxa or aza; and $R^2$ is hydroxylamino or, when taken together with $R^1$ and the imino to which it is attached, forms a five-membered heterocyclic ring such as Δ²-pyrrolinyl, Δ²-imidiazolinyl, Δ²-oxadiazolinyl, Δ²-thiadiazolinyl or Δ²-triazolinyl, said heterocyclic ring being optionally C-substituted with one or two methyl, carboxamido, hydroxy, carbomethoxy or carbethoxy groups and optionally having further ring unsaturation.

Preferred active ingredients of formula 1 are those in which $R^2$ with $R^1$ forms a Δ²-pyrrolinyl or a Δ²-imidazolinyl ring.

Also, included in this invention as active ingredients are the nontoxic, stable salts of the compounds of formula I with acids known to the art to be useful for such purposes, for example, the hydrochloride, sulfate, sulfamate, phosphate, nitrate or acetate salts. The salt form is formed by reacting a base compound of formula I with an excess of an acid in an organic solvent.

The feed compositions of this invention comprise the normal feed rations of the meat producing animals supplemented by a quantity of an active ingredient of formula I, which is effective for improving the growth rate or feed efficiency of the animals but which is not toxic or noxious to a degree that the animals will reduce ingestion of the ration. The quantity of the active ingredient will vary, as is known to the art, with factors such as the cost of the ingredient, the species and the size of animal, the relative activity of the compound of formula I or the type of feed ration used as the basal feed.

Representative feed rations for swine and poultry are in the examples presented hereafter. Swine feed from weanling to fattening or finishing rations may be supplemented. Swine eat from about 0.9 kg per day (for a 11 kg pig) to 4 kg per day (for a 66 kg pig). Most rations are comprised of a corn base supplemented with legume silage, wheat bran, oats, barley, molasses or a protein supplement.

Poultry feeds comprise starter rations, broiler rations and laying rations. The rations are usually based on ground corn, corn meal and soybean meal. The broiler rations, often, contain high energy supplements such as added fats, proteins and vitamins. Turkey rations are similar, but comprise only a starting ration and a growing ration. Chickens or pheasants eat from 12–120 grams of feed per day, turkeys twice that much. Estimated intake of feed is dependent on the weight and age of the meat producing animal.

The active ingredients of formula I are mixed uniformly with such feed rations to give supplemented rations which are then fed as to custom. This is, most often, ad libitum. Conveniently, a premix of the supplemental growth promotant of this invention, optionally combined with other supplements known to this art such as an anthelmintic, a nitrogen source or an antibiotic such as virginiamycin or oxytetracycline, is prepared by the manufacturer for sale to the formulators or feed lot operators. The concentration of pyridylheterocycle in the premix is usually from 5–75% by weight or a concentration 100–2000 times greater than that in the complete feed ration. The premix form may be liquid or solid. Premix vehicles are corn oil, cottonseed oil, molasses or distillers solubles to form a liquid premix preparation. Sucrose, lactose, corn meal, ground corn, flour, calcium carbonate or soybean meal are often used as bases for solid premix preparations. The premix composition is, then, mixed uniformly with whole ration which is commonly fed to the target animal. Such premix compositions are included in the term "feed compositions" as used herein.

The concentration of the pyridylheterocycle of formula I in the complete ration is a nontoxic but active quantity chosen, for example, from a range of about 1–100 parts of active ingredient by weight per million parts of whole feed (ppm). Advantageously, a quantity is chosen from the range of 5–50 ppm of a pyridylheterocycle of formula I.

The percentage ratio by weight of active ingredient to feed suggested for this invention is selected from the range of about 0.0001–0.01%.

The method of using compositions of this invention comprises feeding them to growing, monogastric, meat-producing animals, especially swine and poultry, in an effective growth promoting but nontoxic quantity of such a compound having formula I. Other monogastric animals whose digestive tract features fermentation in a cecum or cecum-like chamber are rabbits and horses.

The supplemented feed rations described above are presented to the animal by methods known to the art. Ad libitum feeding in the pasture, pen or growing shed is most convenient to increase the growth rate of the animal and to increase the feed efficiency of the growing operation. Alternatively, the same supplemented feeds may be given to ruminant animals, particularly when the compound of formula I is coated to bypass the upper stomach or rumen.

The following working examples are intended to illustrate this invention. All percentages are by weight. All temperatures are Centigrade.

EXAMPLE 1

A swine ration for growing hogs of 18–45 kilograms body weight is prepared using the following formula:

| | |
|---|---|
| Corn, ground | 78.15% |
| Soybean oil meal, 44% | 17.0% |
| Meat scraps, 50% | 3.0% |
| Oyster shell flavor | 0.4% |
| Bone meal | 0.5% |
| Zinc oxide | 0.01% |
| Vitamin A, B, $B_{12}$ & D | optional |

The ration is supplemented to 100% with 25 ppm of 3,4-dihydro-4-hydroxy-5-(3-hydroxy-2-pyridinyl)-4-methyl-2H-pyrrole-2-carboxamide which is distributed through a premix carrier. The ration is fed, ad libitum, to the penned growing or fattening swine.

EXAMPLE 2

A chicken ration for broilers is prepared using the following formula:

| | |
|---|---|
| Yellow corn meal | 67.35% |
| Soybean oil meal | 24.00% |
| Menhaden fish meal | 6.00% |
| Steamed bone meal | 1.00% |
| Ground limestone | 1.00% |
| Iodized salt | 0.34% |
| 25% choline chloride | 0.13% |
| Vitamin $B_{12}$ | 0.10% |
| Manganese sulfate | 0.02% |
| Vitamin mix | 0.06% |

The ration is supplemented with 10 ppm of 2-amidoximopyridine and fed ad libitum to the chickens.

EXAMPLE 3

In Vitro Swine Procedure

A. Methodology:

A Yorkshire barrow is surgically prepared either with an ileal cannula, which is placed 15 cm. from the ileo-ceco-colic junction, or a cecal cannula, which is placed midway between the apex and origin of the cecum. The animal is fed 4 times daily to restrict intake to 4.5% of body weight in a 30 kg animal or 2.5% of body weight in a 100 kg animal. The swine grower ration is:

| | % w/w |
|---|---|
| Medium ground shelled corn | 70.60 |
| Soybean meal, 44% | 22.00 |
| Dehydrated alfalfa meal, 17% | 4.50 |
| Calcium propionate | 0.15 |
| Vitamin/mineral premix | 2.75 |

Sampling of the material, via the cannula, begins 150–180 minutes following the first morning feeding and continues any time from 30–120 minutes thereafter, depending on the quantity of material needed. The sample is maintained in crushed ice, no cooler than 5°, and is gassed continuously with carbon dioxide. The collected material is filtered. The filtrate is the inoculum used for incubations of the test and control samples. The gassed inoculum, 2.25 ml, is placed in each of the 10 gassed test tubes, each containing 0.75 ml of a nutrient solution and 0.5 mg of each test compound. Four blank control tubes, along with the test compound tubes, are incubated 5 hours at 37° with agitation. Four more killed tubes are included which are mot incubated.

The tubes are each treated with 0.60 ml of a 25% solution of metaphosphoric acid, then, stored at =4° until analysis. Samples are thawed and centrifuged for 25 minutes at 20,000 r.p.m. The supernatent liquid is decanted, sampled for gas chromatography and automatic analyzing. The results are fed into a computer for finishing to give figures in which the blank control value is 100%. Virginiamycin is used as a positive control.

B. Results:

| Compound | % of control values | | | |
|---|---|---|---|---|
| | VFA | LYS | GLU | LAC* |
| (A) 3,4-Dihydro-4-hydroxy-5-(3-hydroxy-2-pyridinyl)-4-methyl-3H—pyrrole-2-carboxamide | | | | |
| (a) 166.7 ppm | 26 | 136 | — | 162 |
| (b) 166.7 | 43 | 142 | 133 | 109 |
| 16.67 | 103 | 82 | 100 | 100 |
| 1.67 | 113 | 75 | 97 | 99 |
| (B) 2-Amidoximopyridine | | | | |
| 166.67 ppm | 98 | 99 | 114 | 111 |
| (C) 2-(1,2,4-Oxadiazolyl-3)pyridine | | | | ° |
| 166.67 ppm | 101 | 110 | 113 | 106 |
| (D) 5,5-Dimethyl-3-(2'-pyridyl)-4,5-dihydro-1H—triazole | | | | |
| 166.67 ppm | 100 | 97 | 105 | 107 |
| (E) 2-(2-Pyridyl)-imidazoline | | | | |
| 166.67 ppm | 101 | — | 107 | 93 |
| (F) Methyl 5-methyl-3-(2'-pyridyl)-4,5-dihydro-1H—triazole-5-carboxylate | | | | |
| 166.67 ppm | 95 | 81 | 93 | 106 |
| 16.67 | 101 | 72 | 102 | 102 |

| Compound | % of control values | | | |
|---|---|---|---|---|
| | VFA | LYS | GLU | LAC* |
| 1.67 | 96 | 47 | 112 | 105 |
| (G) Virginiamycin | | | | |
| 166.67 ppm | 39 | 289 | 153 | 23 |
| 16.67 | 85 | 212 | 153 | 21 |
| 1.67 | 147 | 134 | 131 | 39 |

*VFA refers to the total of volatile fatty acids, namely acetate, propionate, isobutyrate, butyrate, isovalerate and valerate. LYS is lysine, GLU is glucose and LAC is L-lactic acid.

The in vitro data presented above in the fistula test procedure indicate little change in the fermentation in the digestive tract. This fact, taken with the positive growth data present in the next example, may indicate the activity is due to inhibition of anaerobic bacteria in the intestinal tract.

EXAMPLE 4

Chick Growth Study

A. Methodology:

512 day old broiler chicks, selected for weight, health and sex, are housed in an environmentally controlled room with temperature at 37.7° and humidity at 40%. Chicks are fed ad libitum. Water is offered ad libitum. A corn or, preferably rye, basal ration is fed during the acclimation period (days 1 and 2). It is, then, mixed with the compound under test or used as a control on days 3-17. Either 8 or 16 chicks are used for each test or control group.

Basal Rye Diet

| Diet Ingredients | (% w/w) |
|---|---|
| Ground Rye (fine grind) | 54.6 |
| Soybean Meal (49% protein) | 27 |
| Meat & Bone meal (50% protein) | 10 |
| Dehydrated Alfalfa meal | 1.25 |
| Fat, animal | 4 |
| Dried Whey (or lactose) | 1 |
| Ground Limestone | 0.67 |
| Dicalcium Phosphate | 0.50 |
| Iodized salt | 0.23 |
| Vitamin premix | 0.175 |
| Trace mineral premix | 0.25 |
| DL methionine (98%) | 0.25 |
| Choline Chloride (50% aqueous sol.) | 0.150* |

*Since choline is added as a 50% aqueous solution, its percentage in diet is doubled.

B. Results:

| Chemical | % of Control | |
|---|---|---|
| | Weight (17 day) | Feed/Gain (3-17 day) |
| (A) Virginiamycin | | |
| 10 ppm (rye) | 107.1 | 96.5 |
| 50 | 127.8 | 88.5 |
| 10 | 97.7 | 100.4 |
| (B) 3,4-Dihydro-4-hydroxy-5-(3-hydroxy-2-pyridinyl)-4-methyl-2H—pyrrole-2-carboxamide | | |
| 25 ppm | 109.4 | 92.6 |
| 4.5 | 101.0 | 98.4 |
| 25 | 108.5 | 99.9 |
| (C) 2-Amidoximopyridine | | |
| 10 ppm | 108.5 | 97.0 |
| 10 | 99.2 | 101.2 |
| 50 | 103.0 | 97.3 |
| (D) 2-(1,2,4-Oxadiazolyl-3)-pyridine | | |
| 8.5 ppm | 102.3 | 99.2 |
| (E) 5,5-Dimethyl-3-(2'-pyridyl)-4,5-dihydro-1H—triazole | | |
| 9 ppm | 103.5 | 97.2 |
| 50 | 97.7 | 103.1 |
| (F) 2-(2-Pyridyl)-imidazoline | | |
| 50 ppm | 106.2 | 93.0 |
| (G) Methyl 5-methyl-3-(2'-pyridyl)-4,5-dihydro-1H—triazole-5-carboxylate | | |
| 50 ppm | 108.1 | 91.0 |

These tests illustrate improved weight gain and feed efficiency at doses from 4.5-50 ppm over a range of structural variations of the active ingredients.

EXAMPLE 5

Chemical Preparations (A) 2-(2-Pyridyl)-imidazoline

5 Grams of 2-thiocarboxamidopyridine and 10 ml of ethylene diamine were mixed and heated to 130° for 3 hours. The solution was then cooled and poured into 300 ml of water. It was extracted into ether and dried. Evaporation provided an oil which solidified on trituration with ether. It was filtered and dried, to provide 1.85 g (20%) of a solid, m.p. 97.5°-98.5° C. (lit. 98.5°-99° C.). This solid was sublimed to repurify; m.p. 96.5°-98.5° C.

| Elemental | (Calc.): | C,65.28; | H,6.16; | N,28.55 |
|---|---|---|---|---|
| | (Found): | C,65.38; | H,6.36; | N,27.61 |

(B) 5,5-Dimethyl-3-(2'-pyridyl)-4,5-dihydro-1H-triazole 8.3 Grams (80 mM) of 2-cyanopyridine was dissolved in 80 ml absolute ethanol and placed in a 250 ml round-bottom flask. 20 Ml of hydrazine hydrate (90%) in 30 ml of ethanol was added to it in one portion and stirred at room temperature for 5 hours. TLC (15:35 chloroform/n-pentane on silica gel) showed no starting material. The reaction mixture was then treated with 25 ml acetone and stirred for 1 hour. It was concentrated to about 100 ml, when a yellow precipitate formed. The latter was washed with water and filtered, to give 9.5 g (65%) yellow crystals. They were dried in vacuo overnight, after which the melting point was 95°-97° C.

IR: 3300°-3400° cm$^{-1}$ (N-H stretch).

NMR: 7.0-8.6 (complex multiplet, aromatic, 4H); 6.2 (broad, exchangeable with $D_2O$, amine, 2H); 2.05, 2.1 (sharp singlets, methyls, 6H).

Elemental: (Calc.): C, 61.34; H, 6.86; N, 31.79. (Found): C, 61.43; H, 6.86; N, 31.84.

(C) 2-(1,2,4-Oxadiazolyl-3)pyridine 10.96 Grams (0.08M) of pyridine 2-amidoxime in 100 ml chloroform was treated with 8.34 ml (0.088M) acetic anhydride and 12.4 ml triethylamine. This reaction mixture was stirred at room temperature overnight. The mixture was concentrated to 20 ml when a precipitate formed. This precipitate, O-acetyl pyridine 2-amidoxime, was filtered and dried in vacuo. It was used directly in the next step.

O-Acetyl pyridine 2-amidoxime, 14.0 g (0.08M), in 25 ml glacial acetic acid was heated at reflux temperature for 4 hours. TLC (4:1:1 n-butanol:water:acetic acid) showed no starting material, only a new spot of RF 0.5. Reaction mixture was neutralized with sodium-bicarbonate, decolorized with charcoal and evaporated to dryness. 8.5 Grams (66%) of a crystalline solid was obtained, which was recrystallized from ether and hexane to provide a solid with melting point 89°–90° C.

Elemental (Calc.): C, 59.62; H, 4.38; N, 26.07. (Found): C, 59.61; H, 4.43; N, 26.12.

(D) Methyl 5-methyl-3-(2'-pyridyl)-4,5-dihydro-1H-triazole-5-carboxylate 8.3 Grams (80 mM) of 2-cyanopyridine, dissolved in 80 ml absolute ethanol, was placed in a 250 ml round-bottom flask. 20 Ml hydrazine hydrate (90%) in 30 ml ethanol was added to it in one portion and stirred at room temperature for 5 hours. TLC (15:35, chloroform/n-pentane on silica gel) showed no starting material. The reaction mixture was concentrated to half the volume to yield a yellow-white solid in solution. Methylene chloride (90 ml) was added and the solution was refluxed. Methyl pyruvate (8.17 g, 0.08M) in 20 ml methylene chloride was added to it in drops over 45 minutes. The yellow-orange solution was stirred at reflux overnight. It was then cooled in ice and filtered to provide a bright yellow solid. The latter was crystallized from methanol and diethyl ether to provide 5.6 g (30%) product, m.p. 111°–113° C.

IR: 3400–3450 cm$^{-1}$ (single peak, N-H stretch); 1740–1725 cm$^{-1}$ (intense, ester carbonyl).

NMR: δ7-2-8.6 (complex multiplets, aromatics, 4H); δ6.5 (broad, exchangeable with D$_2$O, amines, 2H); δ3.8 (sharp singlet, methyl ester, 3H); δ2.3 (sharp singlet, methyl, 3H).

Elemental (Calc.): C, 54.54; H, 5.49; N: 25.44. (Found): C, 54.70; H, 5.49; N, 25.31.

(E) 2-Amidoximopyridine 20.8 Grams (0.2 mole) of 2-cyanopyridine was mixed with 14 g (0.2 mole) hydroxylamine hydrochloride and 16.8 g (0.2 mole) sodium bicarbonate in 250 ml water and then was heated on a steam bath for 30 minutes. A crystalline precipitate formed which was filtered, washed with water and dried in vacuo overnight at 40° C. over phosphorous pentoxide. 13.3 G. (50%) white crystalline solid was obtained, m.p. 116°–118° C. TLC (4:1:1, n-Butanol/water/acetic acid) showed a single spot.

IR and NMR data support the proposed structure.

Elemental (Calc.): C, 52.55; H, 5.15; N, 30.64. (Found): C, 52.42; H, 5.15; N, 30.58.

What is claimed is:

1. An animal feed composition supplemented by a quantity of a compound of the formula:

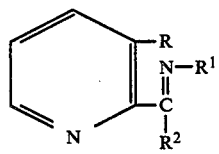

in which:
R is hydrogen or hydroxy;
R$^1$ is hydrogen or, when also attached to R$^2$, methylene, oxa or aza; and
R$^2$ is hydroxylamino or, when taken together with R$^1$ and the imino to which it is attached, forms a five-membered heterocycle, wherein the five-membered heterocycle is Δ$^2$-imidazolinyl, Δ$^2$-oxadiazolinyl, Δ$^2$-thiadiazolinyl or Δ$^2$-triazolinyl, the heterocycle being optionally C-substituted with one or two methyl, carboxamido, hydroxy, carbomethoxy or carbethoxy groups;

or a nontoxic, stable salt thereof, which is effective for increasing the growth rate or feed efficiency of a meat producing monogastric animal but which is nontoxic to the animal.

2. The composition of claim 1 in which the quantity of the compound is selected from the range of from about 1 to about 100 parts of compound per million parts of composition by weight.

3. The composition of claim 2 in which the quantity of the compounds is present in from about 5 to about 50 parts of compound per million parts of composition by weight.

4. The composition of claim 1 in which the compound is 2-amidoximopyridine.

5. The composition of claim 1 in which the compound is 2-(1,2,4-oxadiazolyl-3)-pyridine.

6. The composition of claim 1 in which the compound is methyl 5-methyl-3-(2'-pyridyl)-4,5-dihydro-1H-triazole-5-carboxylate.

7. A method of increasing weight gain or feed efficiency in a meat-producing animal comprising administering orally to the animal an effective therefor, nontoxic quantity of a compound of the formula:

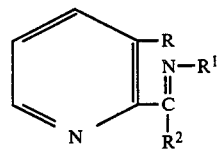

in which:
R is hydrogen or hydroxy;
R$^1$ is hydrogen or, when also attached to R$^2$, methylene, oxa or aza; and
R$^2$ is hydroxylamino or, when taken together with R$^1$ and the imino to which it is attached, forms a five-membered heterocycle, wherein the five membered heterocycle is Δ$^2$-pyrrolinyl, Δ$^2$-imidazolinyl, Δ$^2$-oxadiazolinyl, Δ$^2$-thiadiazolinyl or Δ$^2$-triazolinyl, the heterocycle being optionally C-substituted with one or two methyl, carboxamido, hydroxy, carbomethoxy or carbethoxy groups;

or a nontoxic, stable salt thereof, which is effective for increasing the growth rate or feed efficiency of a meat producing monogastric animal but which is nontoxic to the animal.

8. The method of claim 7 in which the compound is fed in the form of an animal feed ration containing from about 1 to about 100 parts of compound per million parts of ration by weight.

9. The method of claim 7 in which the compound in 3,4-dihydro-4-hydroxy-5-(3-hydroxy-(3-hydroxy-2-pyridinyl)-4-methyl-2H-pyrrole-2-carboxamide.

10. The method of claim 7 in which the compound in 2-amidoximopyridine.

11. The method of claim 7 in which the compound is 2-(1,2,4-oxadiazolyl-3)-pyridine.

12. The method of claim 8 in which the compound contains from about 5 to about 50 parts of compound per million parts of ration by weight.

* * * * *